(12) United States Patent
Kanemoto

(10) Patent No.: US 10,737,089 B2
(45) Date of Patent: Aug. 11, 2020

(54) ELECTRODE PACKAGE AND SEALING APPARATUS

(71) Applicant: Nihon Kohden Corporation, Shinjuku-ku, Tokyo (JP)

(72) Inventor: Michio Kanemoto, Tokyo (JP)

(73) Assignee: Nihon Kohden Corporation, Shinjuku-ku, Tokyo (JP)

( * ) Notice: Subject to any disclaimer, the term of this patent is extended or adjusted under 35 U.S.C. 154(b) by 155 days.

(21) Appl. No.: 15/757,906

(22) PCT Filed: Aug. 26, 2016

(86) PCT No.: PCT/JP2016/003911
§ 371 (c)(1),
(2) Date: Mar. 6, 2018

(87) PCT Pub. No.: WO2017/043038
PCT Pub. Date: Mar. 16, 2017

(65) Prior Publication Data
US 2018/0243548 A1    Aug. 30, 2018

(30) Foreign Application Priority Data

Sep. 7, 2015   (JP) ................................ 2015-175340
Aug. 3, 2016   (JP) ................................ 2016-153154

(51) Int. Cl.
*A61N 1/04*   (2006.01)
*B29C 65/18*  (2006.01)
(Continued)

(52) U.S. Cl.
CPC ........... *A61N 1/0404* (2013.01); *A61N 1/046* (2013.01); *A61N 1/3904* (2017.08); *B29C 65/18* (2013.01);
(Continued)

(58) Field of Classification Search
CPC .... A61N 1/0404; A61N 1/3904; A61N 1/046; A61N 1/0488; A61N 1/69; A61N 1/0472;
(Continued)

(56) References Cited

U.S. PATENT DOCUMENTS 5,402,884 A   4/1995  Gilman et al.
5,579,919 A   12/1996 Gilman et al.
(Continued)

FOREIGN PATENT DOCUMENTS

WO   95/11843 A1   5/1995

OTHER PUBLICATIONS

Int. Search Report dated Jan. 16, 2017 issued by the Int. Searching Authority in Application No. PCT/JP2106/003911 (PCT/ISA/210).
(Continued)

*Primary Examiner* — Paula J Stice
(74) *Attorney, Agent, or Firm* — Sughrue Mion, PLLC

(57) ABSTRACT

An electrode package includes an electrode pad to be attached to a subject, the electrode pad having a gel layer, a lead wire having one end electrically coupled to the gel layer, and a packaging cover having an opening portion, the opening portion being sealed such that the electrode pad and a part of the lead wire are housed inside the packaging cover. A sealing width in at least a part of a section where the packaging cover is sealed together with the lead wire is narrower than a sealing width in a section where only the packaging cover is sealed. A sealing apparatus is configured to seal the packaging cover.

7 Claims, 11 Drawing Sheets

(51) Int. Cl.
 *B29C 65/38* (2006.01)
 *B29C 65/00* (2006.01)
 *A61N 1/39* (2006.01)
 *B29L 31/00* (2006.01)
 *B65B 7/28* (2006.01)
 *B65B 51/10* (2006.01)

(52) U.S. Cl.
 CPC .......... *B29C 65/38* (2013.01); *B29C 66/3494* (2013.01); *B29C 66/43121* (2013.01); *B29C 66/69* (2013.01); *B29C 66/71* (2013.01); *B29C 66/8322* (2013.01); *B29C 66/91431* (2013.01); *B29C 66/91443* (2013.01); *B29C 66/91951* (2013.01); *A61N 1/39* (2013.01); *B29C 66/1122* (2013.01); *B29C 66/53261* (2013.01); *B29C 66/73921* (2013.01); *B29C 66/81431* (2013.01); *B29L 2031/753* (2013.01); *B65B 7/2878* (2013.01); *B65B 2051/105* (2013.01)

(58) Field of Classification Search
 CPC ............ A61N 1/0492; B29C 66/43121; B29L 2003/753
 See application file for complete search history.

(56) References Cited

U.S. PATENT DOCUMENTS

| 6,048,640 A | 4/2000 | Walters et al. |
| 2014/0073896 A1* | 3/2014 | Hyatt ................ A61B 5/04087 600/391 |

OTHER PUBLICATIONS

Written Opinion dated Jan. 16, 2017 issued by the Int. Searching Authority in Application No. PCT/JP2106/003911 (PCT/ISA/237).

* cited by examiner

[Fig. 1]
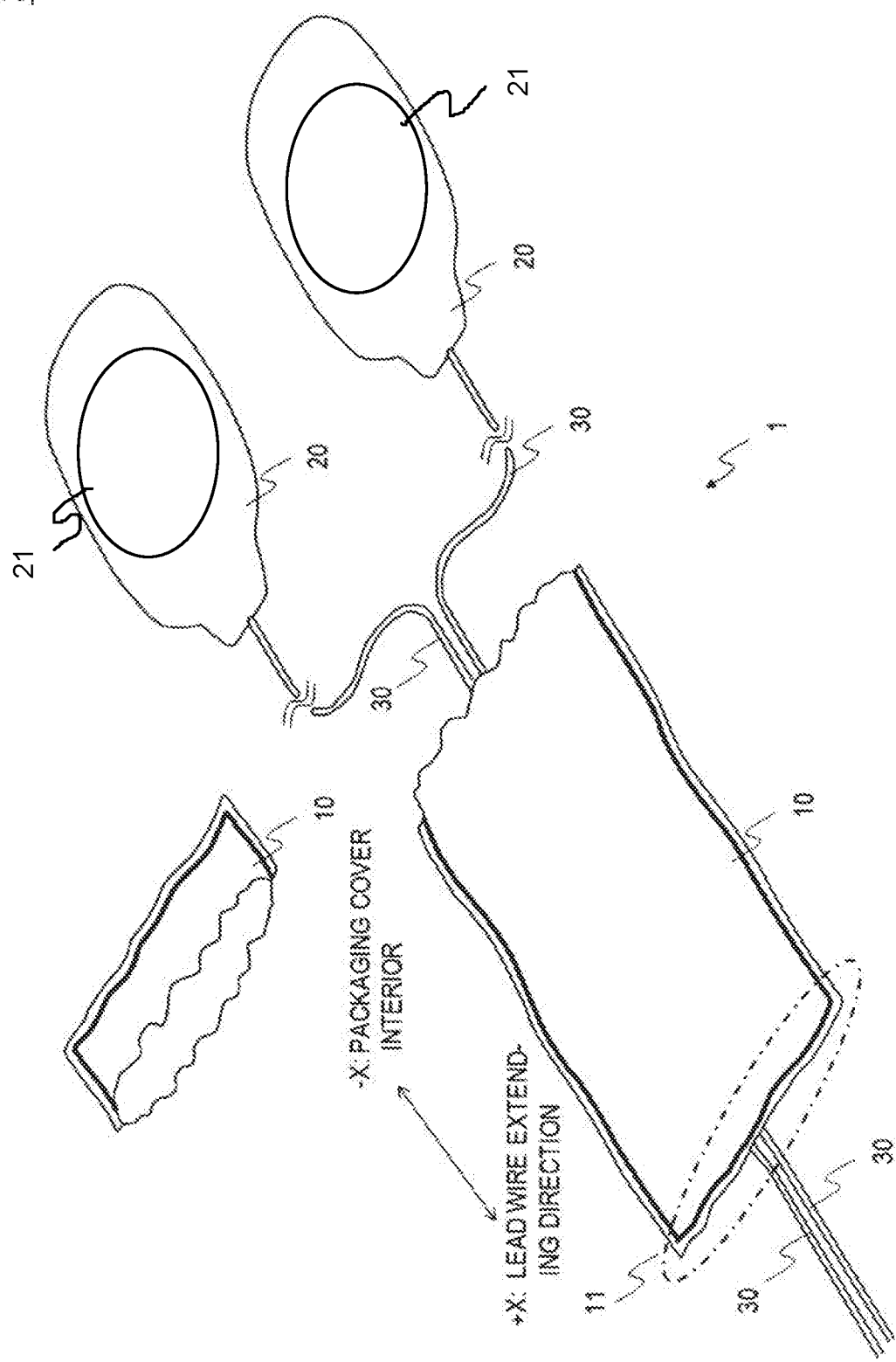

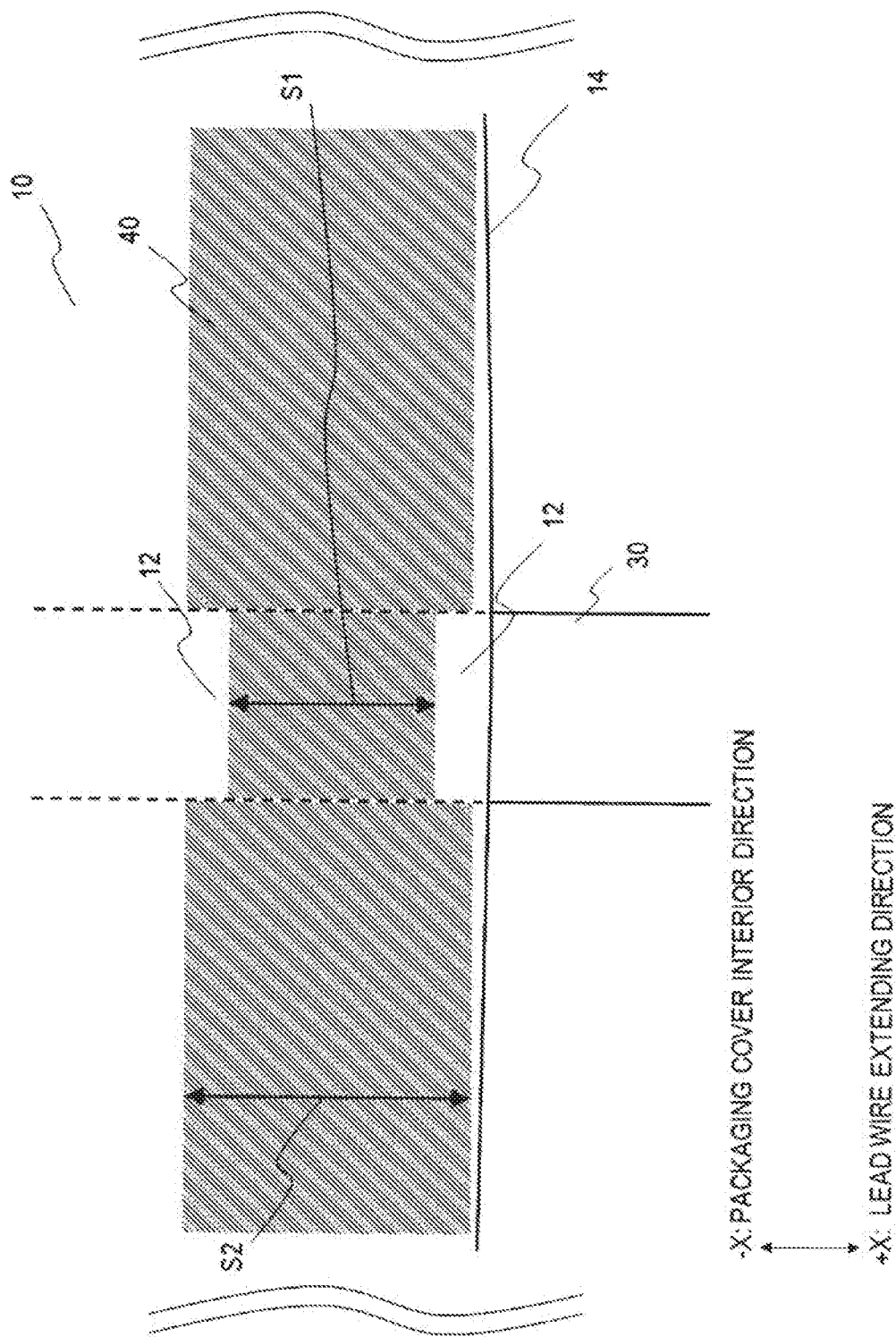
[Fig. 2]

[Fig. 3]
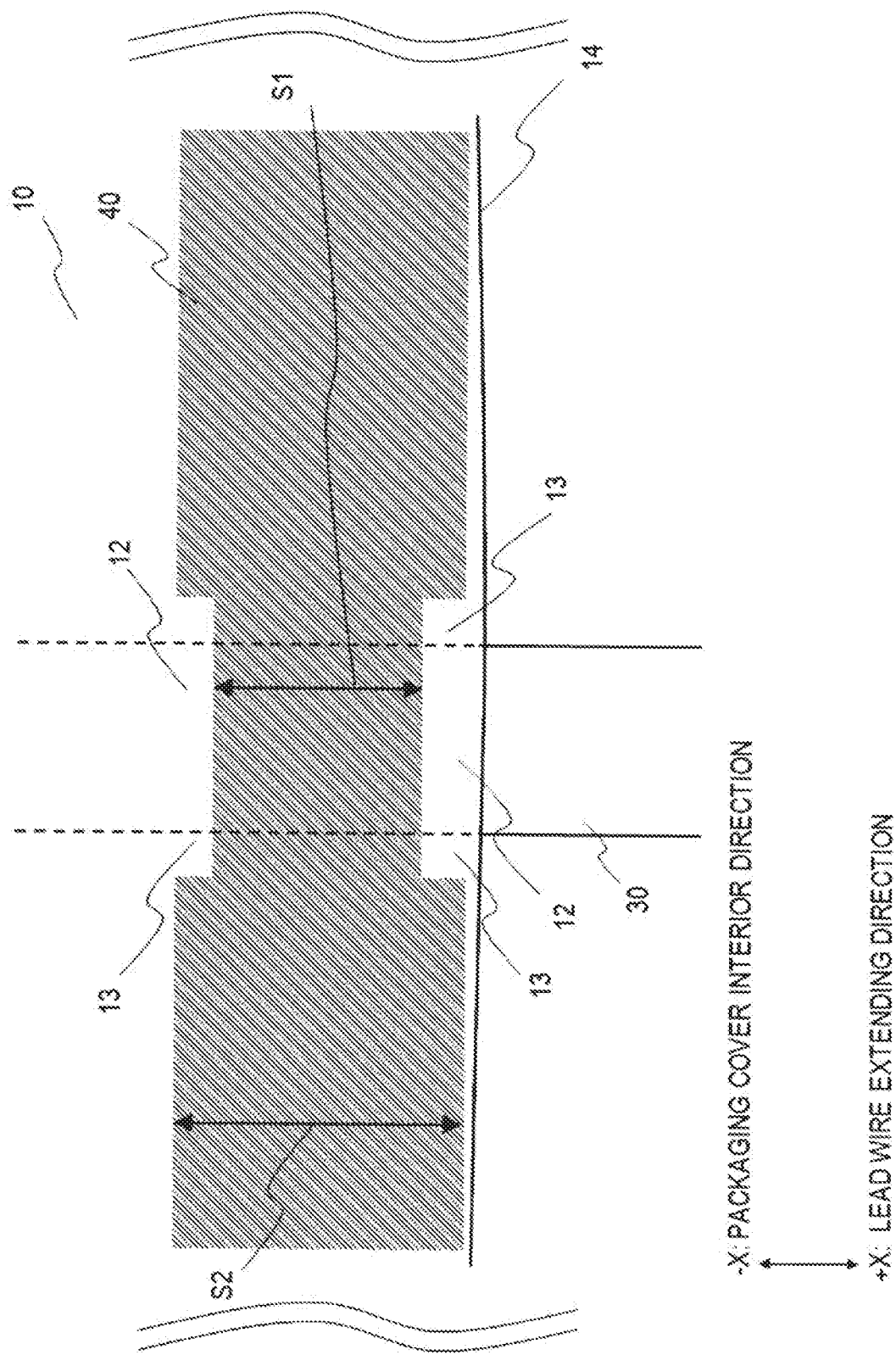

[Fig. 4]
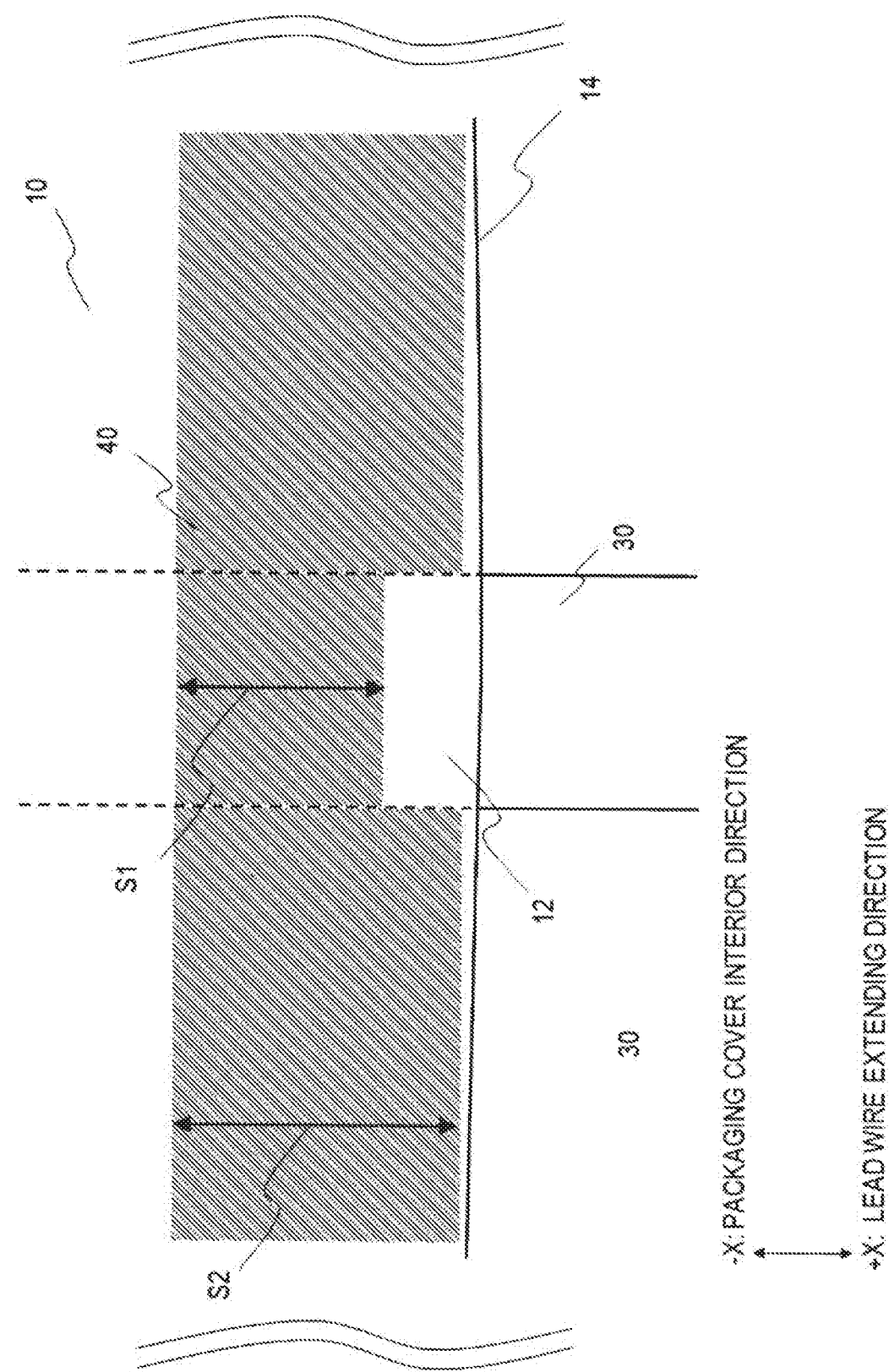

[Fig. 5]
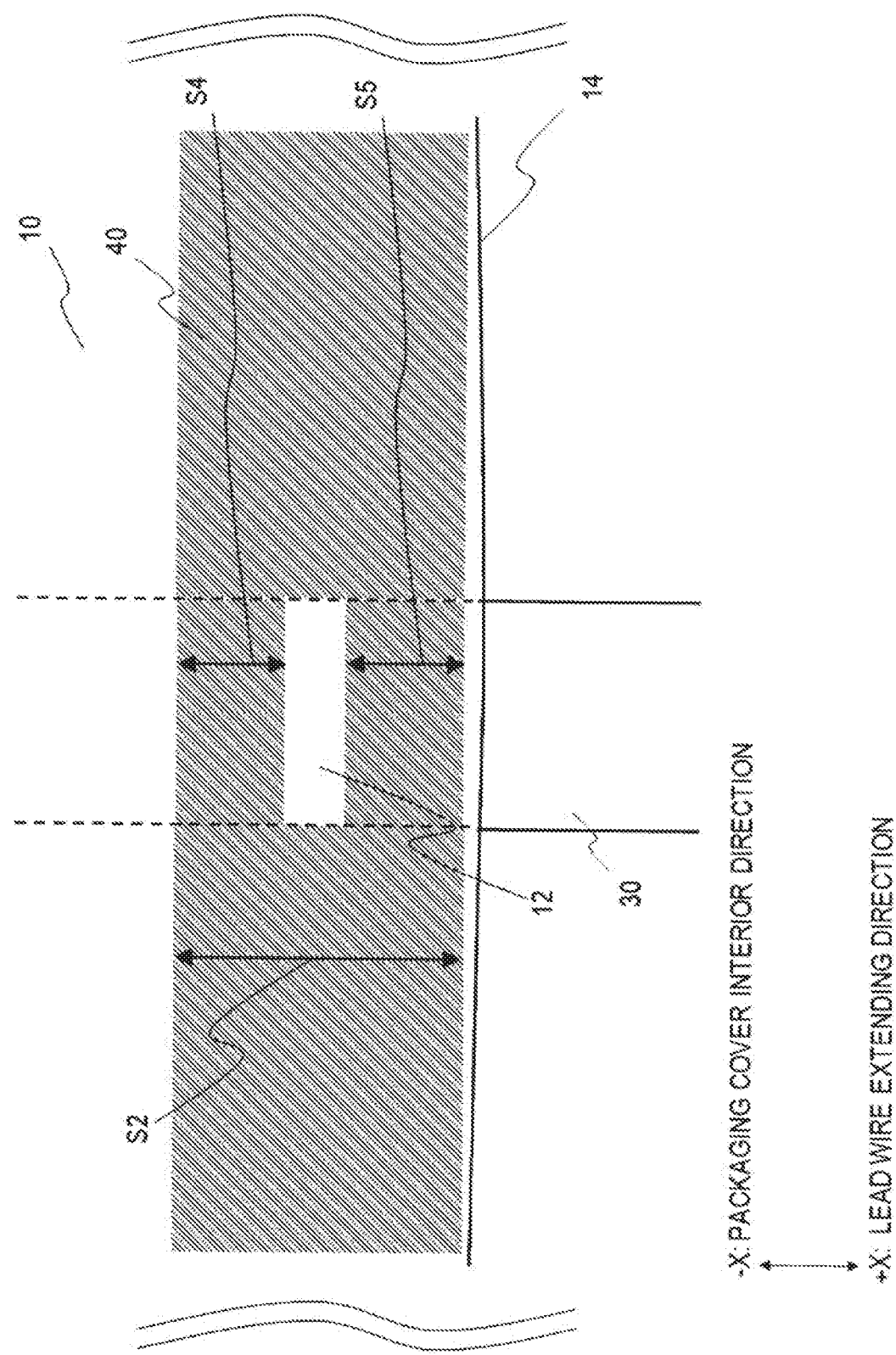

[Fig. 6]
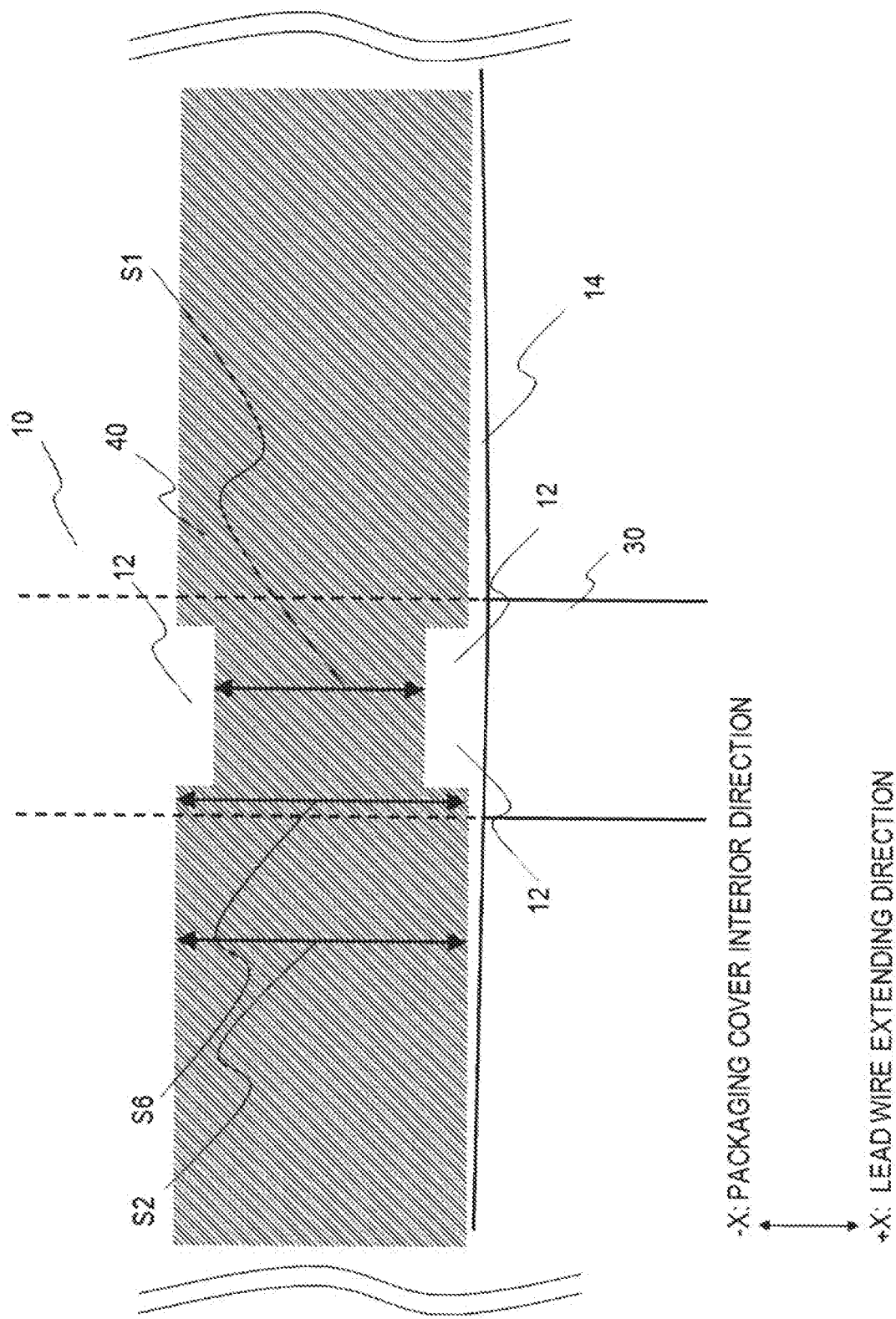

[Fig. 7]
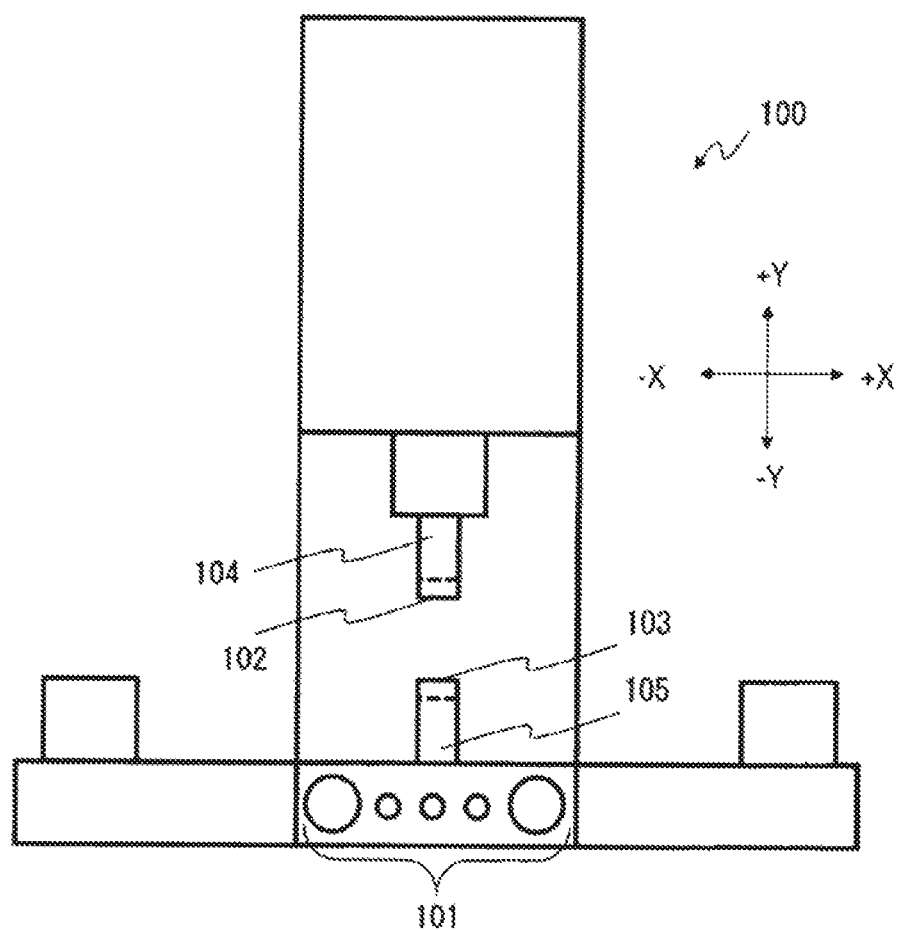

[Fig. 8]
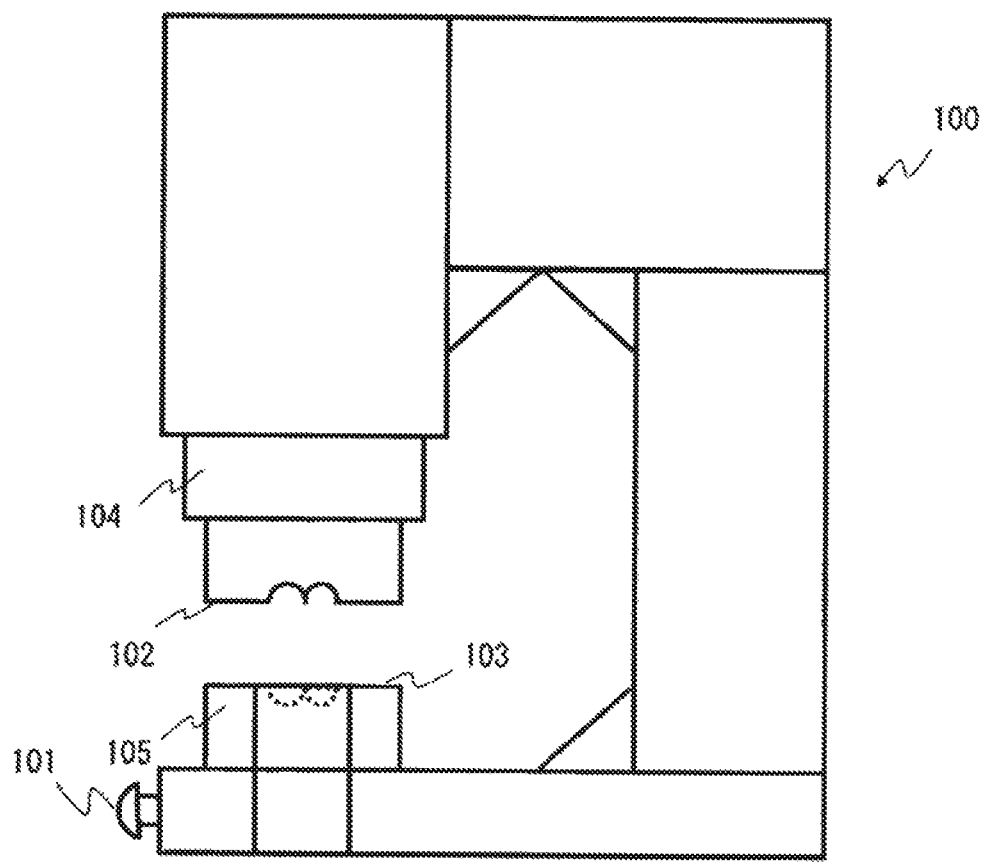

[Fig. 9]
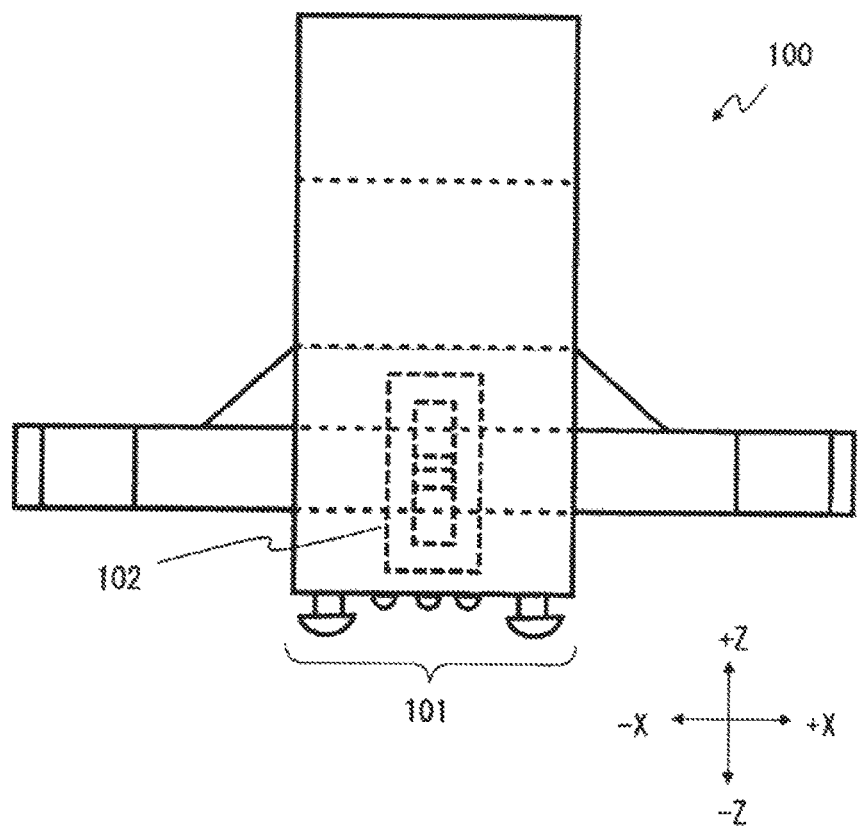
[Fig. 10]
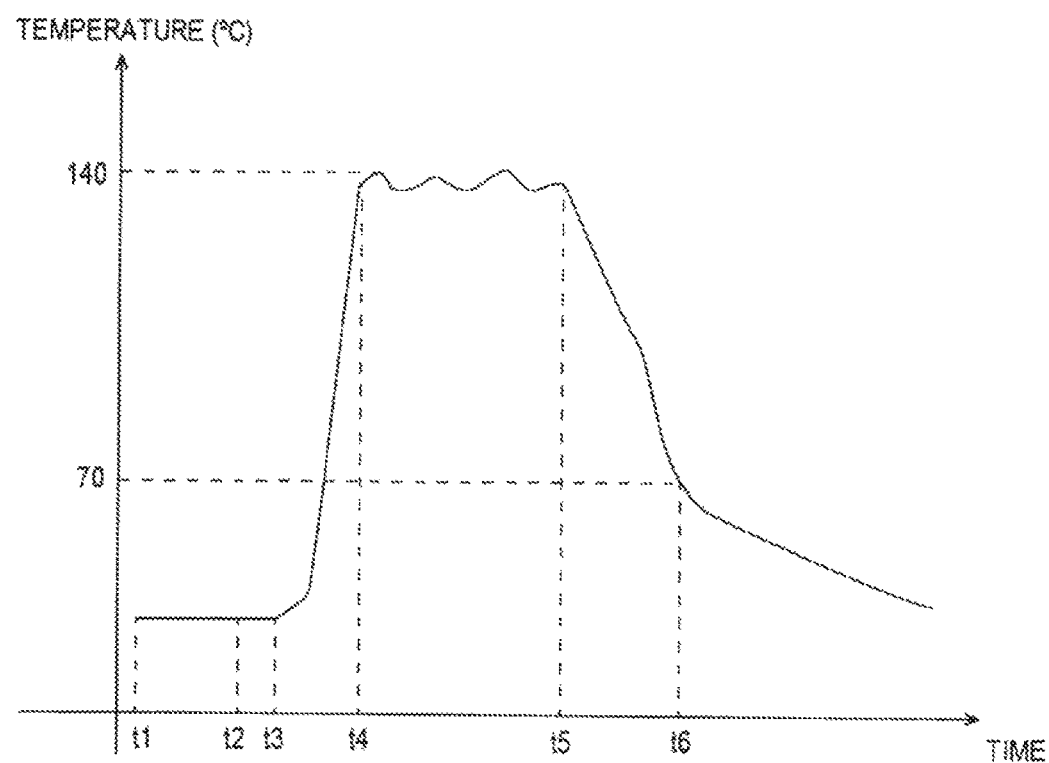

[Fig. 11A]
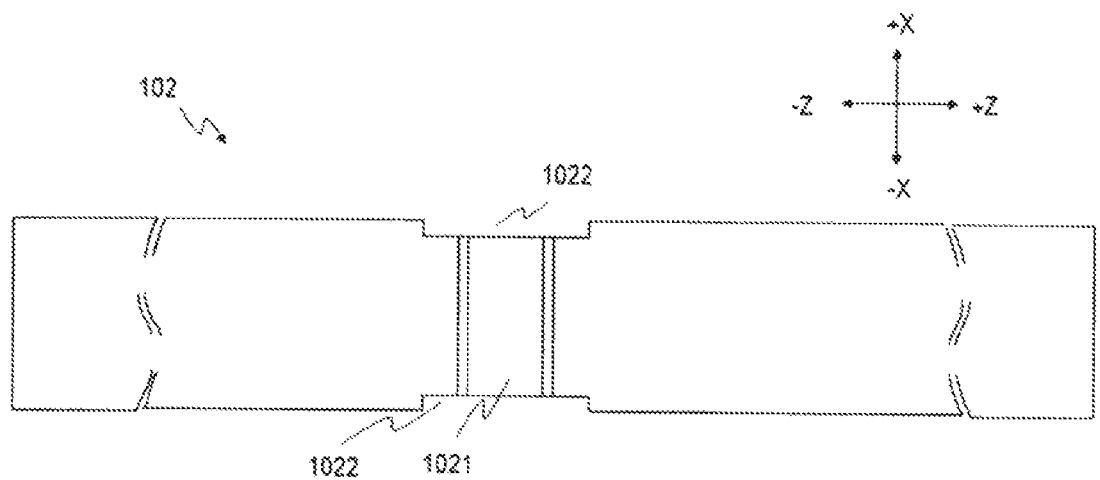
[Fig. 11B]
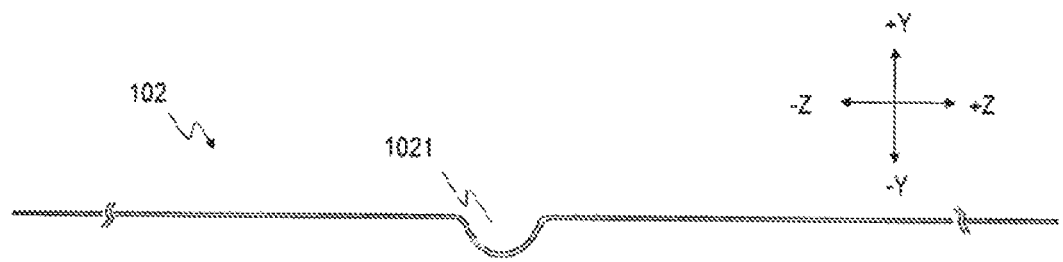

[Fig. 12]
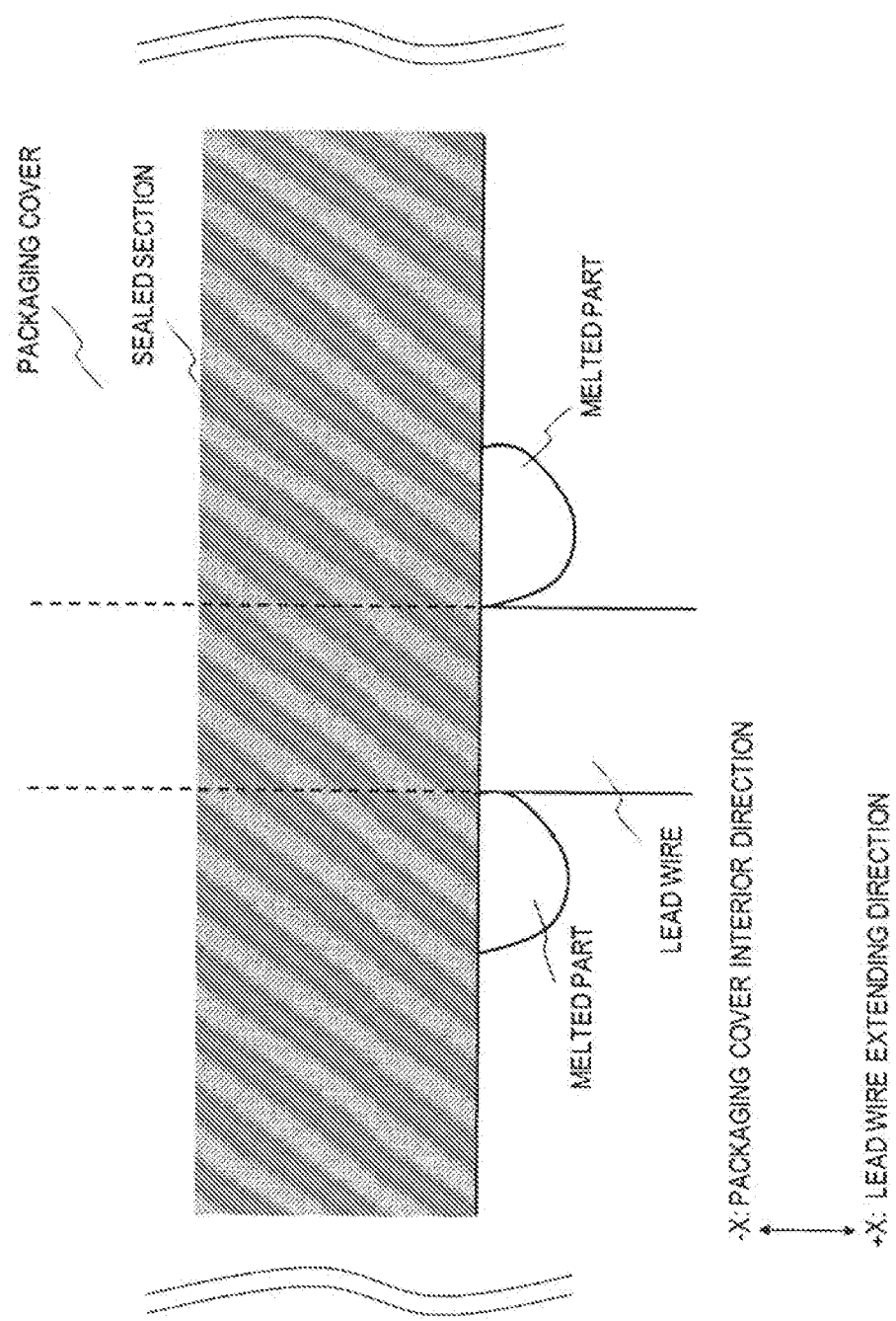

ELECTRODE PACKAGE AND SEALING APPARATUS

TECHNICAL FIELD

The present invention relates to an electrode package used for a defibrillator such as an automated external defibrillator (AED), and a sealing apparatus for scaling the electrode package.

BACKGROUND ART

An AED is a medical device for applying an electric shock (defibrillation) to a subject in ventricular fibrillation to bring the heart of the subject back to a normal condition. The AED has a main device configured to generate such an electric shock, and electrode pads to be attached to a human body. The electrode pads can also be used for defibrillators used in hospitals and the like.

Because the AED is required to be used quickly, various measures are taken to allow its quick use. For example, the AED is stored in a storage case in a state in which the main device and the electrode pads are connected to each other in advance (pre-connection). In order to implement the pre-connection, an electrode package is provided. The electrode package includes a packaging cover and connector-equipped lead wires extending outside from the packaging cover. That is, one ends of the lead wires are connected to the electrode pads, and parts of the lead wires and the electrode pads are housed and stored inside the sealed packaging cover. The other parts of the lead wires extend outside from the inside of the packaging cover.

A sealing apparatus, such as an impulse sealer, is used to seal up the lead wires and the electrode pads inside the packaging cover. The sealing apparatus seals an opening portion of the packaging cover in a state in which the electrode pads and the parts of the lead wires are housed inside the packaging cover. In this manner, it is possible to produce the electrode package in which the other parts of the lead wires extend outside from the inside of the packaging cover.

There are some related art for such an electrode package in which parts of lead wires and electrode pads are housed inside a packaging cover. For example, U.S. Pat. No. 5,579,919A discloses a package in which electrode pads are housed in a packaging cover. U.S. Pat. No. 5,402,884A discloses a system for packaging electrode pads used for defibrillation. U.S. Pat. No. 6,048,640A discloses an electrode package in which a packaging cover is pressed and heated to be sealed, and a method for manufacturing the electrode package.

Related art electrode packages are manufactured such that an opening portion of a packaging cover is sealed in a state in which parts of lead wires extend outside the packaging cover. To perform the sealing, the sealing apparatus presses and heats the packaging cover (film) and then cools it to seal the packaging cover. Generally, there is a slight variation in thickness among the lead wires. Therefore, the thickness (seal diameter) of a seal is made slightly narrower than the diameter of each of the lead wires. A thick diameter of lead wire may cause a coating of the lead wire that has been pressed and heated to be melted to partially protrude from the packaging cover, thereby giving a feeling of insecurity to a user (or may cause the user to misunderstand that it is defective). FIG. 12 is a view illustrating such melted parts. In FIG. 12, an enlarged view of a sealed section for the lead wires is illustrated. As shown in FIG. 12, the melted parts of the cables protrude from the packaging cover. These melted parts protruding from the packaging cover gives a negative feeling to the user.

SUMMARY

Illustrative aspects of the present invention provide an electrode package in which an effect of melting of a lead wire of the electrode package is small.

According to an illustrative aspect of the present invention, an electrode package includes an electrode pad to be attached to a subject, the electrode pad having a gel layer, a lead wire having one end electrically coupled to the gel layer, and a packaging cover having an opening portion, the opening portion being sealed such that the electrode pad and a part of the lead wire are housed inside the packaging cover. A sealing width in at least a part of a section where the packaging cover is sealed together with the lead wire is narrower than a sealing width in a section where only the packaging cover is sealed.

BRIEF DESCRIPTION OF DRAWINGS

FIG. 1 is a view illustrating a configuration of an electrode package according to an exemplary embodiment of the present invention.

FIG. 2 is a view illustrating an example of a structure for sealing an opening portion of the electrode package.

FIG. 3 is a view illustrating another example of a structure for sealing the opening portion of the electrode package.

FIG. 4 is a view illustrating another example of a structure for sealing the opening portion of the electrode package.

FIG. 5 is a view illustrating another example of a structure for sealing the opening portion of the electrode package.

FIG. 6 is a view illustrating another example of a structure for sealing the opening portion of the electrode package.

FIG. 7 is a front view illustrating a configuration of a sealing apparatus according to an exemplary embodiment of the present invention.

FIG. 8 is a side view illustrating a configuration of the sealing apparatus.

FIG. 9 is a top view illustrating a configuration of the sealing apparatus.

FIG. 10 is a chart illustrating a temperature change of a heater of the sealing apparatus.

FIG. 11A is a view illustrating a configuration of the heater.

FIG. 11B is another view illustrating a configuration of the heater.

FIG. 12 is a view illustrating a sealing structure of a related art electrode package.

DESCRIPTION OF EMBODIMENTS

Hereinafter, exemplary embodiments of the present invention will be described with reference to the drawings. Same elements illustrated in the drawings are denoted by same reference signs respectively, and duplicate description thereof will be omitted.

FIG. 1 is an overall view of an electrode package 1 according to an exemplary embodiment of the present invention. The electrode package 1 has a packaging cover 10, electrode pads 20, lead wires 30, and a connector (not shown). To illustrate the internal structure of the electrode package 1, a state in which a portion of the packaging cover 10 is torn apart is shown in FIG. 1.

In the electrode package 1, parts of the lead wires 30 and the electrode pads 20 are sealed up and housed inside the packaging cover 10. As shown in FIG. 1, the other parts of the lead wires 30 extend outside the packaging cover 10. As shown in FIG. 1, a direction in which the lead wires 30 extend outside the packaging cover 10 is referred to as "+X direction (lead wire extension direction)", and an opposite direction to the +X direction (lead wire extension direction) is referred to as "−X direction (packaging cover interior direction)".

As shown in FIG. 1, the electrode pads 20 having the same configuration are provided in a pair. The electrode pads 20 are attached to a surface of a body of a subject (e.g., a patient) mainly when a defibrillator such as an automated external defibrillator (AED) is in use. Each of the electrode pads 20 is provided with a conductive gel layer 21 to be attached to a surface of a body of a subject, an electrode layer which contacting the gel layer 21 to obtain biological signals from the body of the subject, and a non-conductive sheet which is provided on a back side of the gel layer 21. Although not shown in FIG. 1, figures illustrating how to attach the electrode pad 20 may be printed on the non-conductive sheet.

The lead wires 30 are provided for the electrode pads 20 respectively. Each of the lead wires 30 is a cable which electrically connects the defibrillator (e.g., the AED) and the electrode pad 20 to each other. Specifically, one ends of the lead wires 30 are electrically coupled to the gel layers of the electrode pads 20 respectively. In addition. the other ends of the lead wires 30 are connected to the connector (not shown) serving as a connection portion to the defibrillator.

The connector (not shown) is a connection portion which electrically connects the defibrillator and the lead wires 30 (hence the electrode pads 20) to each other. Through the connector (not shown), a voltage can be applied from the defibrillator to the electrode pads 20 when the defibrillator is in use. The connector (not shown) may be a connection mechanism which has general pins (or pin insertion ports).

The electrode pads 20 and the parts of the lead wires 30 are housed inside the packaging cover 10. For example, the packaging cover 10 may be made of polyethylene terephthalate (PET). The packaging cover 10 may contain polyethylene or Himilan (registered trademark). As will be described later, an opening portion 11 is sealed by a sealing apparatus (pressed and heated from opposite sides of the packaging cover) after the electrode pads 20 and the parts of the lead wires 30 are housed inside the packaging cover 10. In this manner, a sealed electrode package 1 is formed.

Next, the sealed opening portion 11 (indicated as a one-dot chain line portion in FIG. 1) will be described in detail. In the sealed opening portion 11, a sealing width in one section where the lead wires 30 and the packaging cover 10 are sealed together is narrower than a sealing width in the other section (a sealing width in a section where only the packaging cover 10 is sealed). Various forms may be provided as opening portions 11 having the property. Configuration examples of the sealed opening portions 11 will be described as follows.

FIG. 2 is an example of an enlarged view of the opening portion 11 in FIG. 1 (the one-dot chain line portion in FIG. 1). In FIG. 2, a downward direction is the +X direction (lead wire extension direction) and an upward direction is the −X direction (packaging cover interior direction). In FIG. 2, each lead wire 30 inside the packaging cover 10 is denoted by a dotted line. In addition, in FIG. 2, a sealed section 40 (a part where the packaging cover 10 is fixed) is hatched by oblique lines. An edge portion 14 of the packaging cover 10 is an outer edge of the packaging cover 10. Although one lead wire 30 is connected to each of the electrode pads 20 in the illustrated example, two or more lead wires 30 may be connected to each of the electrode pads 20.

As shown in FIG. 2, a sealing width (S1 in FIG. 2) in one section where the lead wires 30 and the packaging cover 10 are sealed together is narrower than a sealing width (S2 in FIG. 2) in the other section where only the packaging cover 10 is sealed. Here, the scaling widths mean entire widths in the sealed sections. In the configuration in FIG. 2, the sealing width (S1 in FIG. 2) in the section where the lead wires 30 and the packaging cover 10 are sealed together is narrower on the opposite sides in the −X direction (the packaging cover interior direction, upward direction in FIG. 2) and the +X direction (the lead wire extension direction, which is the downward direction in FIG. 2). In other words, the sealing width (S1 in FIG. 2) in the section where the lead wires 30 and the packaging cover 10 are sealed together is narrowed to be set back from the opposite sides.

As shown in FIG. 2, the sealing width in the section where the lead wires 30 and the packaging cover 10 are sealed together is narrower than the sealing width in the other section. Accordingly, spaces 12 are generated inside the packaging cover 10. The spaces 12 are located at portions close to places where the lead wires 30 are melted. Therefore, melted parts of the lead wires 30 can be retained in the spaces 12. In this manner, it is possible to avoid protrusion of the melted parts of the lead wires 30 from the packaging cover 10.

The sealing widths are not limited particularly. However, the sealing width (S1) in the section where the lead wires 30 and the packaging cover 10 are sealed together may be about 5 mm and the scaling width (S2) in the other section where only the packaging cover 10 is sealed may be about 6 mm. A ratio between the sealing width (S1) in the section where the lead wires 30 and the packaging cover 10 are scaled together and the sealing width (S2) in the other section where only the packaging cover 10 is sealed may be about 1:1.1 to 1:1.5.

FIG. 3 is an enlarged view of another example of the opening portion 11 in FIG. 1 (the one-dot chain line portion in FIG. 1). In the example shown in FIG. 3, a sealing width in parts of the section where only the packaging cover 10 is sealed is also narrowed. That is, the scaling width is also narrowed in parts (spaces 13 in FIG. 3) of the section where only the packaging cover 10 is sealed. Also in such a form, spaces 12 are generated in the vicinities of the section where the lead wires 30 and the packaging cover 10 are sealed together.

FIG. 4 is an enlarged view of another example of the opening portion 11 in FIG. 1 (the one-dot chain line portion in FIG. 1). In the example, configuration is made such that a sealing width in a section where the lead wires 30 and the packaging cover 10 are scaled together is narrower only in the +X direction (the lead wire extension direction, which is a down direction in FIG. 4). Thus, a larger space 12 than that in the examples of FIG. 2 or FIG. 3 is provided between the edge portion 14 of the packaging cover 10 and a sealed section 40. Due to the larger space 12 being provided, melted parts of the lead wires 30 can be retained in the packaging cover 10 in a more reliable manner.

FIG. 5 is an enlarged view of another example of the opening portion 11 in FIG. 1 (the one-dot chain line portion in FIG. 1). In the example, a space 12 where scaling (fixation) is not performed is provided inside a sealed section 40 in which the lead wires 30 and the packaging cover 10 are scaled together. Also in this case, a scaling width (S4+S5) in one section where the lead wire 30 and the packaging cover 10 are sealed together is narrower than a sealing width (S2) in the other section where only the packaging cover 10 is sealed.

In the foregoing description, the examples where the sealing width in the entire section where the lead wires 30 and the packaging cover 10 are sealed together is narrower than the sealing width in the other section have been described (in FIGS. 2 to 5). However, any configuration may be made as long as the sealing width in at least a part of the section where the lead wires 30 and the packaging cover 10 are sealed together is narrower than the sealing width in the other section (the section where only the packaging cover 10 is sealed). Such an example is shown in FIG. 6. In FIG. 6, a sealing width (S1) in a part of the section where the lead wires 30 and the packaging cover 10 are sealed together is narrower than a sealing width in the section where only the packaging cover 10 is sealed. In FIG. 6, the section where the lead wires 30 and the packaging cover 10 are sealed together includes parts (S6) each having the same sealing width as that in the other section. However, spaces 12 into which melted parts of the lead wires 30 can be retained are also provided in the configuration. Thus, a fixed effect can be obtained.

Next, advantages of the electrode package 1 will be described. As described above, the sealing width in the section where the packaging cover 10 is sealed together with the lead wires 30 is narrower than the sealing width in the section where only the packaging cover 10 is sealed. Due to the narrowed sealing width, the space 12 into which the melted parts of the lead wires 30 can be retained is provided. Thus, it is possible to retain the melted parts of the lead wires 30 in the packaging cover 10, thereby avoiding a fear that the melted parts may give a feeling of insecurity to a user (or may cause the user to misunderstand that they are defective). In addition, it is also passible to avoid an event that the protruding melted parts may be obstacles when separating the electrode pads 20 from the packaging cover. That is, it is possible to provide the electrode package 1 in which an effect of melting of the lead wires 30 is reduced.

The configuration in which the sealing width in the entire section where the lead wires 30 and the packaging cover 10 are sealed together is narrower than the sealing width in the other section (the sealing width in the section where only the packaging cover 10 is sealed) is more preferable (FIGS. 2 to 5). This makes it possible to ensure sufficient space 12 to avoid an effect of melting of the lead wires 30 in a more reliable manner.

Next, a configuration example of a sealing apparatus 100 configured to seal the packaging cover 10 of the electrode package 1 will be described. FIGS. 7 to 9 are views illustrating an external configuration of the sealing apparatus 100 viewed from three different sides. FIG. 7 is a front view of the sealing apparatus 100. As shown in FIG. 7, a direction of a horizontal axis when the sealing apparatus 100 is viewed from the front is set as an X-axis direction. In addition, a direction of a vertical axis when the sealing apparatus 100 is viewed from the front is set as a Y-axis direction (an upward direction is set as a +Y direction and a downward direction is set as a −Y direction in FIG. 7). Various input/output interfaces 101 (such as a button, a knob, a setting bar, and an indication lamp for indicating an operating state) are provided in a lower portion of a front surface of the sealing apparatus 100. A heater 102 is provided in an upper portion of the sealing apparatus 100. To seal the opening portion 11, the heater 102 moves in the −Y direction to press and heat the opening portion 11 between the heater 102 and a heater 103. Each of the heaters 102, 103 may be a metal plate etc. having a small thermal expansion coefficient, for example, in a temperature range of from 100° C. to 200° C. After pressing and heating the opening portion 11, the heaters 102, 103 press the opening portion 11 to cool the opening portion 11.

A sealing method using the scaling apparatus 100 will be described. A user places the opening portion 11 on the heater 103 in the lower portion of the sealing apparatus 100 in a state in which parts of the lead wires 30 and the electrode pads 20 are housed inside the packaging cover 10. Then, the sealing apparatus 100 holds the opening portion 11 between the upper heater 102 and the lower heater 103. The heaters 102, 103 press and heat the opening portion 11 from the opposite sides. The pressed place becomes the sealed section 40. The lead wires 30 and polyethylene, Himilan (registered trademark) etc. contained in the interior of the packaging cover 10 are pressed and heated to be thereby melted. After being pressed and heated, the melted sealed section 40 is cooled to be thereby coagulated. Thus, the opening portion 11 is sealed in the state in which the lead wires 30 are interposed.

FIG. 8 is a side view of the sealing apparatus 100. A depth direction (a horizontal direction in FIG. 8) of the sealing apparatus 100 is set as a Z-axis direction. The sealing apparatus 100 has the heater 102 which is disposed in the upper portion of the apparatus and the heater 103 which is provided in a position in the lower portion of the apparatus correspondingly to the heater 102. In addition, the sealing apparatus 100 has a temperature control unit (not shown) for performing temperature control of the heaters 102, 103. That is, the sealing apparatus 100 is configured to control the temperatures of the heaters 102, 103 ((heating and cooling) to perform sealing.

During the sealing, the heater 102 moves in the −Y direction so that the heaters 102, 103 press the opening portion 11 between the heaters 102, 103 and along the opening portion 11 to heat the opening portion 11. The opening portion 11 is then cooled to implement the sealing. The heaters 102, 103 may both move during the sealing to press the opening portion 11 between the heaters 102, 103 and along the opening portion 11.

FIG. 9 is a view of the sealing apparatus 100 from top. As shown in FIG. 9, the heater 102 is provided to extend in the Z-axis direction. Although not shown, the heater 103 is provided in a position opposed to the heater 102.

The heaters 102, 103 will be described more in detail. The heater 102 is attached to a seal bar 104. The seal bar 104 may have a function of fixing the heater 102 and cooling the heater 102. Similarly, the heater 103 is attached to a seal bar 105. The seal bar 105 may also have a function of fixing the heater 103 and cooling the heater 103. A flow of a sealing process of an impulse sealer provided with a temperature control function will be described as follows. First, the heaters 102, 103 start pressing the opening portion 11 such that the opening portion 11 is held between the heaters 102, 103. After holding the opening portion 11, electric current is applied to the heaters 102, 103 to start heating. After a given period of time, the heaters 102, 103 terminate the heating. The opening portion 11 is then cooled after the heating is terminated. The heaters 102, 103 release the pressing. Thus, the electrode package 1 in which the opening portion 11 is sealed is formed.

An operation example of the impulse sealer provided with the temperature control function will be further described with reference to FIG. 10. FIG. 10 is a graph showing the relationship between an elapsed lime since Stan of the sealing process and temperature change of the heaters 102, 103. The sealing process is started at a time t1. The heater 102 starts moving (time t1) and the heaters 102, 103 start pressing (time t2). Electric current is applied to the heaters 102, 103 so that the heaters 102, 103 start heating the opening portion 11 (time t3). After the start of the heating, the temperature of the heaters 102, 103 soon reaches a preset temperature (140° C. in this example) (time t4). The heaters 102, 103 repeal ON/OFF of the electric current to continue the heating at the preset temperature for a given period of time (time period from t4 to t5). Then, the heaters 102, 103 terminate the heating (time t5). After the heating is terminated, the opening portion 11 is cooled (time period from t5 to t6). When the temperature of the opening portion 11 becomes a fixed temperature (70° C. in this example) or lower, the sealing apparatus 100 terminates the pressing (time t6). Thus, the electrode package 1 in which the opening portion 11 is sealed is formed.

FIGS. 11A and 11B are views illustrating a structure example of the heater 102 corresponding to the opening portion 11 shown in FIG. 2. The heater 102 has a recessed portion 1021 corresponding to the section where the lead wires 30 and the packaging cover 10 are sealed together (FIG. 11A).

The heater 102 further has a narrowed portion 1022 for narrowing a sealing width at the section where the lead wires 30 and the packaging cover 10 are sealed together. That is, the heater 102 has a shape (a constricted part 1022) whose width is partially narrowed. In the following description, the length of the heater 102 in the X-axis direction (the length of the heater 102 in the extending direction of the lead wire 30) is defined as the width of the heater 102. Due to the narrowed portion 1022 being provided, electric resistance in this part (the position for sealing the lead wires 30) increases. The magnitude of the resistance R is inversely proportional to the width of the heater 102 w (R is proportional to l/w) according to the formula of the resistance (R being proportional to L/S in which L denotes a length and S denotes a sectional area). The heating quantity Q is proportional to $IR^2$ according to Joule's law, in which I denotes the current and R denotes the resistance. Accordingly, the heating quantity Q in each part of the heater 102 is inversely proportional to $w^2$ (Q is proportional to $1/w^2$).

A heater width (width in the X-axis direction) in the part of the heater 102 where the narrowed portion 1022 is provided is set at 5 mm and a heater width (width in the X-axis direction) in the other part of the heater 102 is set at 6 mm. Thickness (length in the Y-axis direction) in each part is fixed. That is, the sectional area of the part where the narrowed portion 1022 is provided is narrower than the sectional area of the other part. In this case, a heating quantity Q1 in the part where the narrowed portion 1022 is provided is 1.44 times ((1/25)/(1/36)) as large as a heating quantity Q2 in the part where the narrowed portion 1022 is not provided. By a general sealing apparatus, it is difficult to seal the lead wires 30 once due to shortage of a heating quantity of a heater (heating portion) when there is a variation in thickness among the lead wires 30. Therefore, the general sealing apparatus heats only the lead wires in a first sealing process to thereby mold the thicknesses of the lead wires into a fixed thickness (preforming) or soften the lead wires (preheating) and then seal the packaging cover and the lead wires in a second sealing process. That is, the general sealing apparatus performs sealing twice. On the other hand, according to the sealing apparatus 100 according to the embodiment, the heating quantity Q1 in the part where the narrowed portion 1022 is provided is 1.44 times as large as the heating quantity Q2 in the part where the narrowed portion 1022 is not provided. Accordingly, it is possible to sufficiently heat even the section which requires a larger heating quantity in order to seal the lead wires 30 and the packaging cover 10 together. Thus, the section where the lead wires 30 and the packaging cover 10 are sealed together can be fixed in a reliable manner even when the sealing is performed only once. As described above, the magnitude of the resistance R is inversely proportional to the sectional area (a value depending on the width (length in the X-axis direction) of the heater 102 and the thickness (length in the Y-axis direction) of the heater 102). Therefore, the thickness (dimension in the Y-axis direction) of the heater 102 may be adjusted to adjust the heating quantity in each part of the heater 102.

FIG. 11B is a view showing the structure of the heater 102 similarly to FIG. 11A. As shown in FIG. 11B, the recessed portion 1021 where the lead wires 30 can be disposed is provided. The user performs the sealing process after placing the lead wires 30 on the recessed portion 1021.

Although not shown in the drawings, the heater 103 may have substantially the same configuration as the heater 102. The heaters 102, 103 are configured to hold the packaging cover 10 and the lead wires 30 between the heaters 102, 103.

As described above, the heaters 102, 103, each being partially narrowed in width correspondingly to the lead wires 30, are used to perform the sealing. Since the heating quantity in the narrowed part is higher, the section which requires a higher heating quantity in order to seal the lead wines 30 and the packaging cover 10 together can be sealed in a reliable manner when the lead wires 30 are disposed in the narrowed part. In addition, after making control so that both the section where the lead wires 30 and the packaging cover 10 are sealed together and the other section reach proper temperature, the sealing apparatus 100 can perform heating and cooling. Accordingly, the scaling apparatus 100 can complete scaling by a single process.

While the present invention has been described with reference to certain exemplary embodiments thereof, the scope of the present invention is not limited to the exemplary embodiments described above, and it will be understood by those skilled in the art that various changes and modifications may be made therein without departing from the scope of the present invention as defined by the appended claims.

This application is based on Japanese Patent Application No. 2015-175340 filed on Sep. 7, 2015 and Japanese Patent Application No. 2016-153154 filed on Aug. 3, 2016, the entire contents of which are incorporated herein by reference.

The invention claimed is:

1. An electrode package comprising:
    an electrode pad to be attached to a subject, the electrode pad having a gel layer;
    a lead wire having one end electrically coupled to the gel layer; and
    a packaging cover having an opening portion, the opening portion being sealed such that the electrode pad and a part of the lead wire are housed inside the packaging cover,
    wherein a sealing width in at least a part of a section where the packaging cover is sealed together with the lead wire is narrower than a sealing width in a section where only the packaging cover is sealed, and
    wherein the sealing width extends in a lead wire extension direction that is a direction in which the lead wire extends outside the packaging cover.

2. The electrode package according to claim 1, wherein the sealing width in an entire section where the packaging cover is sealed together with the lead wire is narrower than the sealing width in the section where only the packaging cover is sealed.

3. The electrode package according to claim 1, wherein the electrode package is configured such that the sealing width in the section where the packaging cover is sealed together with the lead wire is narrowed in an extending direction of the lead wire.

4. The electrode package according to claim 1, wherein the electrode package is configured such that the sealing width in the section where the packaging cover is sealed together with the lead wire is narrowed in an extending direction of the lead wire and in an interior direction of the packaging cover.

5. The electrode package according to claim 1, wherein the sealing width in the section where only the packaging cover is sealed is 1.1 to 1.5 times wider than the sealing width in the section where the packaging cover is sealed together with the lead wire.

6. The electrode package according to claim 1, wherein the packaging cover comprises polyethylene terephthalate.

7. The electrode package according to claim 1, wherein the sealing width is defined in a direction from a closest point on an edge of the opening portion of the packaging cover toward an inside of the packaging cover.

\* \* \* \* \*